United States Patent
Hadi

(10) Patent No.: US 8,357,186 B2
(45) Date of Patent: Jan. 22, 2013

(54) BONE BOLT ASSEMBLY FOR ATTACHING SUPPORTING IMPLANTS TO BONES, FOR HOLDING MULTIPLE BONES IN RELATIVE POSITIONS, AND FOR HOLDING TOGETHER FRACTURED BONE FRAGMENTS

(75) Inventor: Bassam A. Hadi, Paducah, KY (US)

(73) Assignee: Bassam A. Hadi, Paducah, KY (US)

( * ) Notice: Subject to any disclaimer, the term of this patent is extended or adjusted under 35 U.S.C. 154(b) by 612 days.

(21) Appl. No.: 12/565,065

(22) Filed: Sep. 23, 2009

(65) Prior Publication Data
US 2011/0071576 A1 Mar. 24, 2011

(51) Int. Cl.
*A61B 17/58* (2006.01)
*A61B 17/84* (2006.01)
*A61B 17/86* (2006.01)
*A61B 17/70* (2006.01)

(52) U.S. Cl. .................. 606/300; 606/246; 606/306
(58) Field of Classification Search .............. 411/383, 411/389, 397, 546; 606/246–263, 278–279, 606/300–301, 304, 328, 57, 105, 277, 282, 606/305–306, 310, 318, 324
See application file for complete search history.

(56) References Cited

U.S. PATENT DOCUMENTS

| | | | |
|---|---|---|---|
| 5,269,784 A | | 12/1993 | Mast |
| 5,562,735 A | * | 10/1996 | Margulies ...................... 601/61 |
| 5,647,710 A | | 7/1997 | Cushman |
| 5,919,194 A | * | 7/1999 | Anderson ..................... 606/313 |
| 6,368,322 B1 | | 4/2002 | Luks et al. |
| 6,592,587 B1 | | 7/2003 | Roger |
| 6,709,213 B2 | | 3/2004 | Bailey |
| 2004/0015172 A1 | * | 1/2004 | Biedermann et al. ........... 606/73 |
| 2004/0122431 A1 | * | 6/2004 | Biedermann et al. ........... 606/73 |
| 2005/0273105 A1 | | 12/2005 | Konieczynski et al. |
| 2007/0118120 A1 | * | 5/2007 | Stevenson et al. .............. 606/61 |
| 2009/0131989 A1 | | 5/2009 | Willert et al. |

OTHER PUBLICATIONS

Eeric Truumees; Lumbar Pedicle Screw Placement; Section X—Posterior Lumbar Approach: Arthrodesis and Instrumentation (date unknown, pp. 156-159).
Author unknown; Pedicle Screw Segmental Instrumentation; The Burton Report (www.burtonreport.com/infspine/SurgStabilPedScrews.htm); date uknown.
Ullrich, Jr., M.D., Peter F.; Pedicle Screws for Spine Fusion; Spine-health (www.spine-health.com/print/treatnnent/spinal-fusion/pedicle-screws-spine-fusion); created Dec. 7, 2007.

* cited by examiner

*Primary Examiner* — Kevin T Truong
*Assistant Examiner* — Larry E Waggle, Jr.
(74) *Attorney, Agent, or Firm* — Thompson Colburn LLP

(57) ABSTRACT

A bone bolt assembly is designed for attaching supporting implants between adjacent bones, for holding adjacent bones relative to each other, and for holding together fractured bone fragments. The functions performed by the bone bolt assembly are achieved without the use of bone screws that are implanted into the bone.

19 Claims, 3 Drawing Sheets

BONE BOLT ASSEMBLY FOR ATTACHING SUPPORTING IMPLANTS TO BONES, FOR HOLDING MULTIPLE BONES IN RELATIVE POSITIONS, AND FOR HOLDING TOGETHER FRACTURED BONE FRAGMENTS

CROSS-REFERENCE TO RELATED APPLICATIONS

None.

STATEMENT REGARDING FEDERALLY SPONSORED RESEARCH OR DEVELOPMENT

Not Applicable.

APPENDIX

Not Applicable.

BACKGROUND OF THE INVENTION

1. Field of the Invention

The present invention pertains to a bone bolt assembly that is designed for attaching supporting implants between adjacent bones, for holding adjacent bones relative to each other, and for holding together fractured bone fragments. These functions performed by the bone bolt assembly are achieved without the use of bone screws that are inserted into the bone that could potentially fracture the bone.

2. Description of the Related Art

Surgical screws are commonly used to hold bones or bone fragments together or attach anatomical body parts to bones. Surgical screws employed in these types of orthopedic procedures are commonly referred to as bone screws.

The typical bone screw is a metal implant screwed into the bone. The bone is prepared by first drilling a hole into the bone where the bone screw is to be implanted. The drilled hole diameter is larger than the minor diameter of the screw and less than the major diameter of the screw. This allows the threads of the screw to cut into the bone surrounding the drilled hole as the screw is advanced through the hole. Bone screws are commonly used to set or hold a bone in position relative to an adjacent bone, to immobilize fractured bone fragments to aid in the healing of the fracture, and to secure an implant in place relative to a bone.

A particular type of bone screw used in spine fusion surgery to hold implants in place is called a pedicle screw. Pedicle screws are implanted into the pedicle of a vertebra to hold supporting rods or plates to the spine. Pedicle screws are commonly implanted in two or more consecutive vertebra segments with a rod or plate connected between the screws to support the section of the spine.

A problem encountered with the use of bone screws implanted in bone is the strength of the connection between the screw and the bone is dependent on the strength of the surrounding bone. If the strength of the bone has been deteriorated due to smoking, disease, or other causes, the portion of the bone surrounding the screw could fracture or split during insertion of the screw.

SUMMARY OF THE INVENTION

The bone bolt assembly of the invention is designed to secure together adjacent bones, bone fragments, and to secure implants to bones without requiring a bone screw to be implanted into the bone. By eliminating the need for a bone screw implanted into the bone, the assembly of the invention avoids the potential problem of bone screws causing fracturing of the bone in and around the location where the assembly is secured to the bone, and also avoids the potential problem of bone screws becoming loose over time.

The bone bolt assembly of the present invention is basically comprised of a tubular member, a guide tip that is removably attached to one end of the tubular member, and a proximal bolt and distal bolt that are removably attached to opposite ends of the tubular member in use of the assembly. Each of these component parts of the assembly is constructed of surgical steel. However, the component parts could also be constructed of other biocompatible materials.

The tubular member is a straight, elongate cylindrical member. An interior bore having internal screw threading extends through the length of the tubular member. In one embodiment, the interior bore is surrounded by internal screw threading that extends the entire length of the bore. In an alternate embodiment, the interior bore and the internal screw threading do not extend entirely through the tubular member. Instead, two separate interior bores having internal screw threading extend short distances into the opposite ends of the tubular member. In a still further embodiment, external screw threading is formed on the exterior of the tubular member and extends along the entire length of the tubular member.

The guide tip has external screw threading at one end and a conical-shaped surface or other equivalent shaped surface at the opposite end. The external screw threading is complementary to the internal screw threading of the tubular member. Screwing the tip external screw threading into the internal screw threading at one end of the tubular member removably attaches the tip to the tubular member.

The proximal and distal bolts are substantially identical in construction. Each has external screw threading at one end and a head at the opposite end. The external screw threading is complementary to the internal screw threading of the tubular member. Each head is adapted for engagement with an appropriate driving tool to rotate the bolt in response to rotating the tool. In addition, each head can be adapted for attachment to a spinal fixation system, for example, a spinal instrumentation rod or a spinal instrumentation plate. In addition, each head could be constructed to swivel or pivot relative to the external screw threading of the bolt.

In use of the assembly, the guide tip is removably attached at one end of the tubular member and the proximal bolt is attached at the opposite end of the tubular member. In an alternate embodiment of the assembly, the proximal bolt could be an integral part of one end of the tubular member.

A straight hole is drilled through the bone, adjacent bones, or bone fragments into which the assembly is to be inserted. The tubular member is inserted guide tip first through the drilled hole. The proximal bolt head prevents the tubular member from passing completely through the drilled hole. The length of the tubular member is determined so that, with the tubular member inserted into the drilled hole to where the proximal bolt head is positioned adjacent the bone, the guide tip attached to the opposite end of the tubular member projects from the drilled hole at the opposite side of the bone, bones, or bone fragments. With this positioning of the assembly, the tip can then be removed from the end of the tubular member and replaced with the distal bolt that is attached to the tubular member after the tip is removed. If needed, spinal instrumentation can then be attached to the tubular member by being attached to the heads of the proximal and distal bolts. In addition, the spinal instrumentation can be attached to the tubular member by being positioned between the opposite ends of the tubular member and the proximal and distal bolts prior to the attachment of the proximal and distal bolts to the tubular member.

In the embodiment of the bone bolt assembly that comprises the tubular member having external screw threading formed on the tubular member along the length of the tubular member, the tubular member is again inserted guide tip first into the drilled hole. The tubular member is advanced through the hole by turning the proximal bolt head with an appropriate tool. The tubular member is advanced through the hole until the tip can be removed from the end of the tubular member and replaced with the distal bolt in the manner described above. The external screw threading of the tubular member grips the bone, bones, or bone fragments.

In the above manner, the bone bolt assembly of the invention is attached to a bone, between adjacent bones or between bone fragments without requiring external screw threading to secure the bone bolt assembly inside the hole drilled through the bone. The bone bolt assembly thereby eliminates the potential problem of fracturing of the bone in and around the location of the bone bolt assembly, or the potential for screw threads backing out of the drilled hole in the bone. If these potential problems are not present, then the embodiment of the bone bolt assembly comprising the tubular member with the external screw threading may be used to secure the tubular member to the bone, bones, or bone fragments.

Other features of the bone bolt assembly are set forth in the following detailed description of the preferred embodiments of the assembly and in the drawing figures.

DETAILED DESCRIPTION OF THE PREFERRED EMBODIMENT

As stated earlier, the basic component parts of the bone bolt assembly comprise a tubular member 10, a guide tip 12, a proximal bolt 14 and a distal bolt 16. Each of these component parts is preferably constructed of surgical steel. However, other biocompatible materials may be used in the component part's construction.

Figure 1:
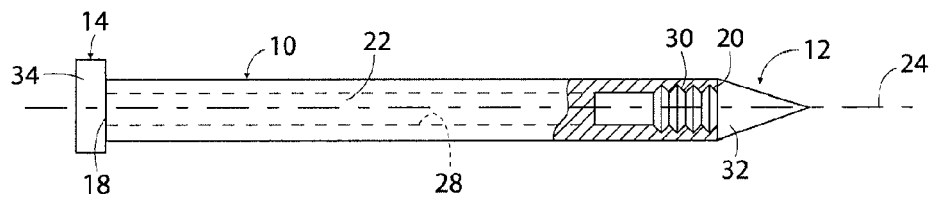
FIG. 1 is a side, partially sectioned view of one embodiment of the bone bolt assembly.
Figure 2:
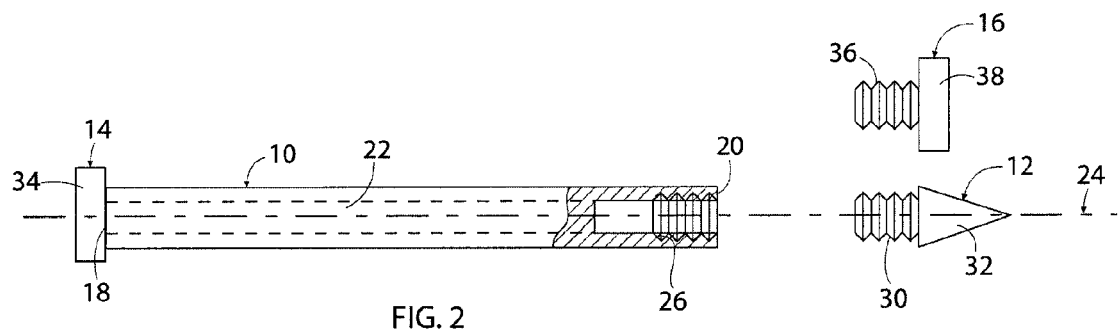
FIG. 2 is a side, partially sectioned view of the assembly shown in FIG. 1 showing the guide tip removed from the tubular member and the distal bolt that replaces the guide tip.
Figure 3:
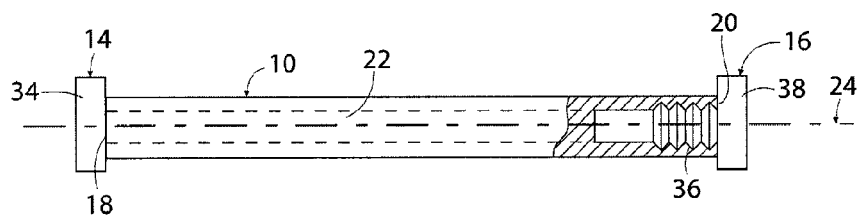
FIG. 3 is a side, partially sectioned view of the assembly showing the tip replaced with a distal bolt.

FIGS. 1-3 show a first embodiment of the assembly that is comprised of the tubular member 10, the guide tip 12, and the distal bolt 16. The size of the component parts shown in the drawing figures is enlarged to facilitate the description of the component parts. In actual use of the bone bolt assembly, the tubular member 10 would typically have a length dimension of about 1½ to 2½ inches and a diameter dimension of about one quarter of an inch. The other component parts would be dimensioned accordingly.

The tubular member 10 shown in FIG. 1 has an elongate, straight length with opposite proximal 18 and distal 20 ends. The tubular member 10 has a smooth, cylindrical exterior surface 22 that extends the entire length of the tubular member. The cylindrical exterior surface 22 has a center axis 24 that defines mutually perpendicular axial and radial directions relative to the bone bolt assembly. In the embodiment shown in FIG. 1, the tubular member 10 has a hollow interior bore defined by internal screw threading 26 that extends a short distance axially into the distal end 20 of the tubular member 10. In an alternate embodiment, the center bore could extend entirely through the length of the tubular member 10 and could have internal screw threading along its entire length, or could have portions of internal screw threading adjacent the opposite proximal 18 and distal 20 ends of the tubular member. The internal bore extending entirely through the tubular member 10 is represented by the dashed lines 28 shown in the drawing figures.

The guide tip 12 has an axial length with external screw threading 30 at one end and a conical-shaped surface 32 at the opposite end. The external screw threading 30 is complementary to the internal screw threading 26 at the tubular member distal end 20. As shown in FIG. 1, the tip 12 is removably attached to the tubular member 10 by screwing the tip external screw threading 30 into the internal screw threading 26 at the tubular member distal end 20. The tip conical-shaped surface 32 has a diameter dimension at its base that is substantially the same as the diameter dimension of the tubular member 10. From the base of the conical-shaped surface 32, the tip extends axially away from the tubular member 10 and tapers to the distal end of the tip 12. Although the tip 12 is shown with a conical-shaped surface 32, other equivalent surface shapes, for example, a parabolic surface shape or a semicircular surface shape, could be provided on the tip 12. It is only necessary that the configuration of the tip surface 32 facilitate guiding the insertion of the tip 12 and tubular member 10 through a hole drilled in a bone or bones.

In the embodiment of the assembly shown in FIG. 1, the proximal bolt 14 is formed as an integral part of the tubular member 10 at the tubular member proximal end 18. The proximal bolt 14 has a head 34 that is shown projecting radially from the tubular member exterior surface 22. In alternate embodiments, the proximal bolt head 34 could have a diameter dimension that is substantially the same as that of the tubular member 10. The proximal bolt head 34 is shown only schematically in the drawing figures. The bolt head 34 is intended to be adapted for attachment to any known type of spinal instrumentation (for example, rods or plates) and thereby attach the instrumentation to the tubular member 10. It is also possible that the bolt head 34 be attached to the tubular member 10 by a connection that enables the bolt head 34 to move (for example, pivot or swivel) relative to the tubular member 10.

The distal bolt 16 has an axial length with external screw threading 36 at one end and a head 38 at the opposite end. The external screw threading 36 is complementary to the internal screw threading 26 at the distal end of the tubular member 10. The head 38 of the distal bolt 16 is substantially the same as the head 34 of the proximal bolt 14.

The assembly of FIGS. 1-3 is intended for use in securing or attaching spinal instrumentation to a bone, in securing together adjacent bones, or in securing together bone fragments. In use of the assembly, a hole is drilled through the bone, adjacent bones or bone fragments. The hole diameter is slightly larger than the exterior diameter of the tubular member 10 and the base of the guide tip 12. With the tip 12 attached to the tubular member distal end 20, the assembly is inserted tip first through the drilled hole. When the assembly is entirely inserted through the drilled hole, the tip 12 is accessible at the opposite end of the bone from which the assembly was inserted. The tip 12 can then be removed from the tubular assembly 10 and replace with the distal bolt 16 that is screwed to the tubular member distal end 20. In this manner, the bone bolt assembly of FIGS. 1-3 is secured to a bone, to adjacent bones, or to bone fragments without requiring external screw threading cutting into bone which could cause fracturing or splitting of the bone around the drilled hole.

Once the assembly of FIGS. 1-3 is in place, if needed, spinal instrumentation can be secured to the proximal bolt head 34 and the distal bolt head 38.

Figure 4:
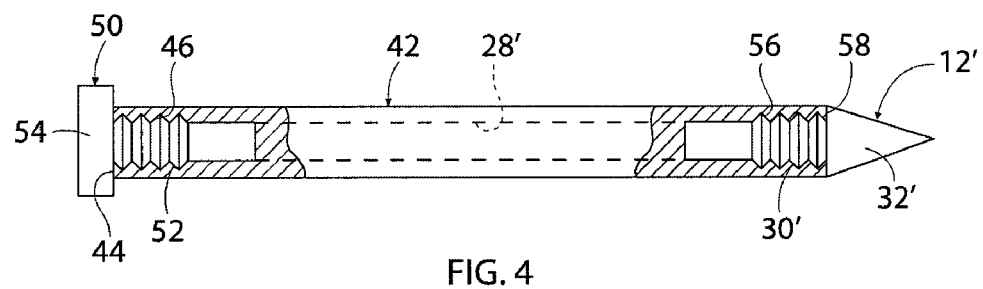
FIG. 4 is a side, partially sectioned view of a further embodiment of the assembly.
Figure 5:
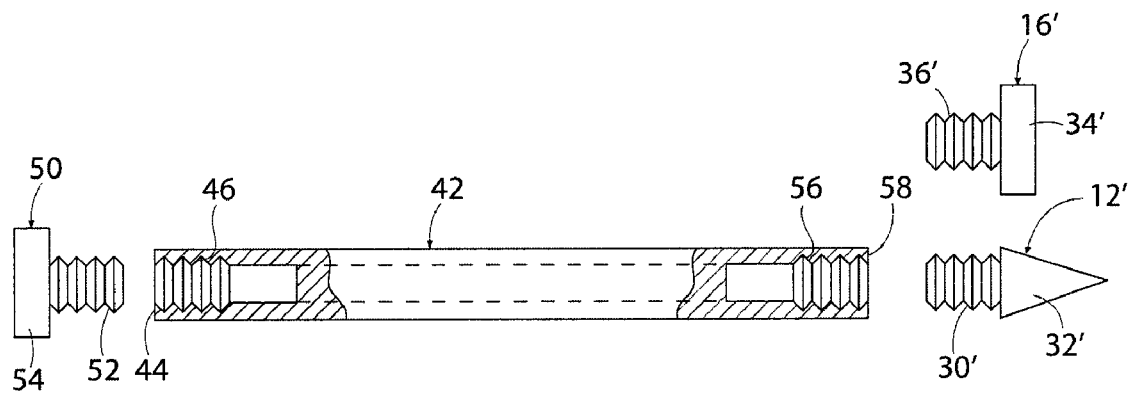
FIG. 5 is a side, partially sectioned view of the assembly shown in FIG. 4 with the proximal bolt and tip removed from the tubular member and showing the distal bolt that replaces the tip.
Figure 6:
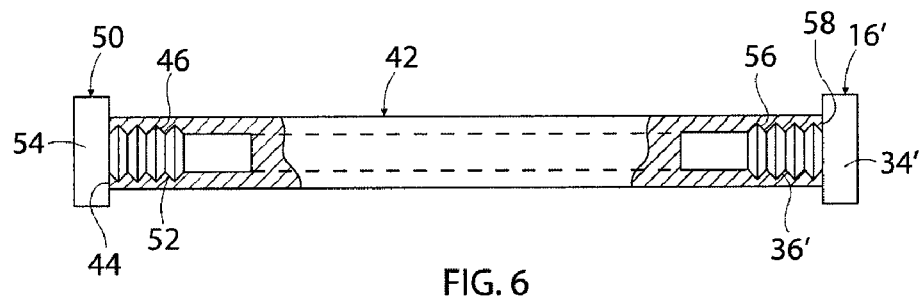
FIG. 6 is a side, partially sectioned view of the embodiment shown in FIG. 5 with the proximal bolt and distal bolt assembled to the tubular member.

FIGS. 4-6 show an alternate embodiment of the bone bolt assembly from that shown in FIGS. 1-3. The embodiment of FIGS. 4-6 employs the same tip 12 and distal bolt 16 of the embodiment of FIGS. 1-3 and therefore the features of these component parts are identified by the same reference numbers used in identifying these features in FIGS. 1-3. However, in FIGS. 4-6 these reference numbers are followed by a prime (').

The tubular member 42 of FIGS. 4-6 is substantially the same as the tubular member 10 of FIGS. 1-3 except for an additional interior bore at the tubular member proximal end 44. The proximal end interior bore is defined by internal screw threading 46 that extends axially into the tubular member 42 from the tubular member proximal end 44. As shown in FIGS. 4-6, the internal screw threading 46 extends only a short distance into the tubular member 42 from the tubular member proximal end 44. As an alternative, the internal screw threading 46 could extend entirely through the interior of the tubular member 44 as represented by the dashed lines 28'. In such an alternate embodiment, the internal screw threading 56 at the tubular member distal end 58 and the internal screw threading 46 at the tubular member proximal end 44 are two portions of the internal screw threading 28' that extends entirely through the length of the tubular member 42.

The embodiment of the bone bolt assembly shown in FIGS. 4-6 also differs from the previously described embodiment of FIGS. 1-3 in that it comprises a separate proximal bolt 50. The proximal bolt 50 has an axial length with external screw threading 52 at one end and a head 54 formed at the opposite end. The external screw threading 52 is complementary to the internal screw threading 46 that extends into the tubular member proximal end 44. By screw threading the proximal bolt external screw threading 52 into the tubular member internal screw threading 46, the proximal bolt 50 is removably attached to the tubular member 42 at the proximal end 44. The head 54 of the proximal bolt 50 has the same construction as the head of both the proximal bolt 14 and the distal bolt 16 described earlier.

The use of the embodiment of the bone bolt assembly shown in FIGS. 4-6 is substantially the same as that of the embodiment of FIGS. 1-3. The only difference is that the proximal bolt 50 is removably attached to the tubular member 42 at the tubular member proximal end 46 with the guide tip 12' being removably attached to the tubular member 42 by screwing the tip external screw threading 28' into the internal screw threading 56 provided at the tubular member distal end 58. With the proximal bolt 50 removably attached to the tubular member 42 and the tip 12' removably attached to the tubular member 42, the assembly is inserted through a hole previously drilled through the bone, bones, or bone fragments and is secured in place in the same manner as the embodiment of FIGS. 1-3 described previously.

Figure 7:
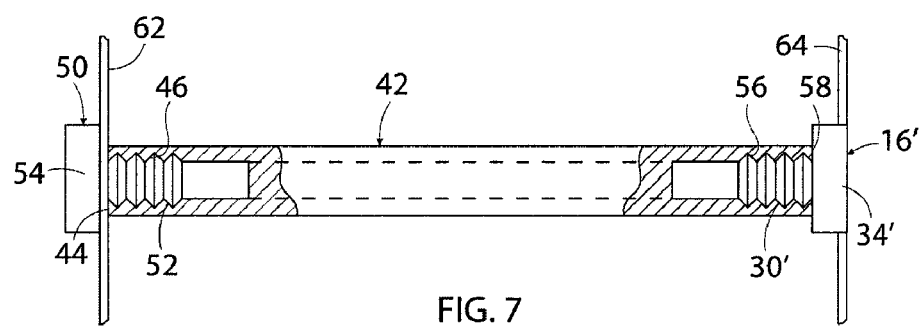
FIG. 7 is a side, partially sectioned view of the embodiment of FIGS. 5 and 6 shown used with spinal instrumentation.

FIG. 7 shows the embodiment of the bone bolt assembly of FIGS. 4-6 with schematic representations of spinal instrumentation 62, 64 removably attached to the assembly. The left side of the assembly shown in FIG. 7 represents a spinal instrumentation 62 that is removably attached to the assembly, or more specifically to the tubular member, 42 by the external screw threading 52 of the proximal bolt 50. The proximal bolt threading 52 is first inserted through an opening provided in the spinal instrumentation 62 before the screw threading 52 is screwed into the internal screw threading 46 at the tubular member proximal end 44. By tightening the proximal bolt 50 to the tubular member 42, the proximal bolt 50 secures the spinal instrumentation 62 to the tubular member 42 of the assembly.

The right side of FIG. 7 shows the schematic representation of spinal instrumentation 64 being removably attached to the tubular member 42 of the assembly by any known attachment mechanism provided on the head 38' of the distal bolt 16'. In this manner, the distal bolt 16' removably attaches the spinal instrumentation 64 to the tubular member 42.

Figure 8:
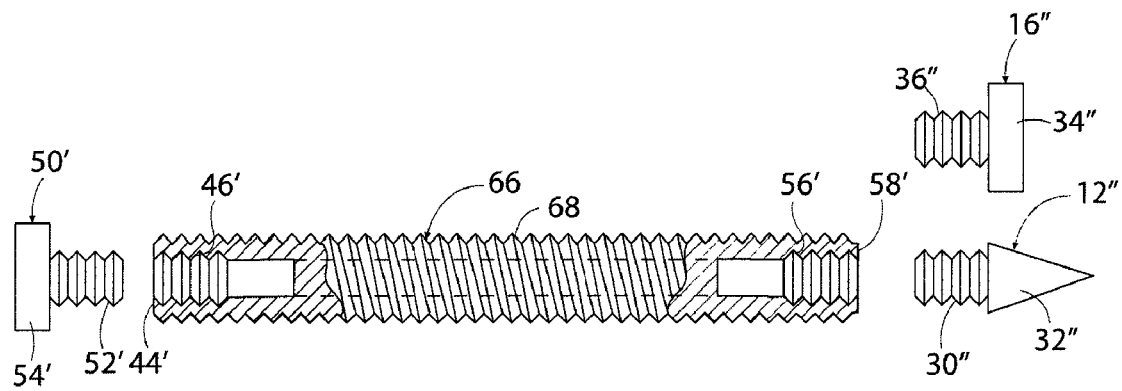
FIG. 8 is a view of the bone bolt assembly similar to that of FIGS. 4-7 but showing an embodiment of the tubular member having external screw threading formed on the tubular member along the length of the tubular member.

FIG. 8 shows a further embodiment of the bone bolt assembly that is substantially the same as that shown in FIGS. 4-7 except for the tubular member 66 having external screw threading 68 that extends along the length of the tubular member. Because all of the component parts of the bone bolt assembly shown in FIG. 8 are the same as those shown in FIGS. 4-7 and described earlier, those component parts will not be described again. The same component parts shown in FIG. 8 are identified by the same reference numbers shown in FIGS. 4-7, with the reference numbers being followed by a prime (') or a double prime (").

The use of the embodiment of the bone bolt assembly shown in FIG. 8 is substantially the same as that of the embodiment shown in FIGS. 4-7. The only difference is that with the proximal bolt 50' removably attached to the tubular member 66 and the tip 12" removably attached to the tubular member 66, the assembly is advanced through a hole previously drilled through the bone, bones, or bone fragments by turning the bolt 50' with an appropriate tool which in turn screw threads the tubular member 66 through the hole due to the external screw threading 68 on the tubular member 66. The tubular member external screw threading 68 secures the tubular member 66 to the bone, bones, or bone fragments. The tubular member 66 is further secured in place in the same manner as the previously discussed embodiments.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A bone bolt assembly designed for attaching supporting plates and rods to bone, to hold adjacent bones stationary relative to each other, and to hold bone fragments together, the bone bolt assembly comprising:

a tubular member having an elongate, straight length with opposite proximal and distal ends, the tubular member having a hollow interior bore defined by a cylindrical interior surface, the interior bore having a center axis that defines mutually perpendicular axial and radial directions relative to the tubular member length, the tubular member interior surface having internal screw threading formed thereon and the tubular member having a smooth cylindrical exterior surface that extends entirely over the tubular member length and is dimensioned for axially directed insertion through a hole drilled in bone;

a head at the proximal end of the tubular member length, the head being adapted for transmitting axial movement of the head to axial movement of the tubular member; and, a tip removably attached to the tubular member at the tubular member distal end, the tip having an axial length with opposite proximal and distal ends, the tip having a cylindrical exterior surface with external screw threading at the tip proximal end, the external screw threading being complementary to the tubular member internal screw threading and the external screw threading being threaded inside the internal screw threading in removably attaching the tip to the tubular member distal end, and the tip having a conical exterior surface at the tip distal end.

2. The bone bolt assembly of claim 1, further comprising:
a bolt that is removably attachable to the tubular member distal end when the tip member is removed from the tubular member distal end, the bolt having an axial length with opposite proximal and distal ends, the bolt having a cylindrical exterior surface with external screw threading at the bolt proximal end, the external screw threading being complementary to the tubular member internal screw threading whereby the bolt external screw threading can be threaded inside the tubular member internal screw threading after the tip member has been removed from the tubular member.

3. The bone bolt assembly of claim 2, further comprising:
the head being adapted for attaching a spinal instrumentation rod to the tubular member.

4. The bone bolt assembly of claim 3, further comprising:
the bolt being adapted for attaching a spinal instrumentation rod to the tubular member.

5. The bone bolt assembly of claim 2, further comprising:
the head being adapted for attaching to a spinal instrumentation plate to the tubular member.

6. The bone bolt assembly of claim 5, further comprising:
the bolt being adapted for attaching to a spinal instrumentation plate to the tubular member.

7. The bone bolt assembly of claim 1, further comprising:
the interior bore extending entirely through the tubular member.

8. The bone bolt of claim 7, further comprising:
the internal screw threading extending entirely through the tubular member interior bore.

9. The bone belt assembly of claim 7, further comprising:
the head closing the interior bore.

10. A bone bolt assembly designed for attaching supporting plates and rods to bone, to hold adjacent bones stationary relative to each other, and to hold bone fragments together, the bone bolt assembly comprising:

a tubular member having an elongate, straight length with opposite proximal and distal ends, the tubular member having a center axis that defines mutually perpendicular axial and radial directions relative to the tubular member, the tubular member having an interior bore with proximal internal screw threading extending axially into the tubular member at the tubular member proximal end and the tubular member having an interior bore with distal internal screw threading extending axially into the tubular member at the tubular member distal end, the tubular member also having a cylindrical exterior surface that extends entirely over the tubular member length and is dimensioned for axially directed insertion through a hole drilled in bone;

a proximal bolt that is removably attached to the tubular member at the tubular member proximal end, the proximal bolt having an axial length with a cylindrical exterior surface with external screw threading at one end and having a head at an opposite end, the external screw threading being complementary to the tubular member proximal internal screw threading and the external screw threading being threaded inside the proximal internal screw threading in removably attaching the proximal bolt to the tubular member at the tubular member proximal end;

a tip that is removably attached to the tubular member at the tubular member distal end, the tip having an axial length with a cylindrical exterior surface and external screw threading at one end and having a conical exterior surface at an opposite end, the tip external screw threading being complementary to the tubular member distal interior screw threading and the tip external screw threading being threaded inside the distal internal screw threading in removably attaching the tip to the tubular member at the tubular member distal end; and, a distal bolt that is removably attachable to the tubular member at the tubular member distal end when the tip is removed from the tubular member distal end, the distal bolt having an axial length with a cylindrical exterior surface with external screw threading at one end and having a head at an opposite end, the external screw threading of the distal bolt being complementary to the tubular member distal internal screw threading and the distal external screw threading being threaded inside the distal internal screw threading in removably attaching the distal bolt to the tubular member at the tubular member distal end.

11. The bone bolt assembly of claim 10, further comprising:
the proximal bolt head and the distal bolt head each being adapted to attach a spinal instrumentation rod to the tubular member.

12. The bone bolt assembly of claim 10, further comprising:
the proximal bolt head and the distal bolt head each being adapted to attach a spinal instrument plate to the tubular member.

13. The bone bolt assembly of claim 10, further comprising:
the interior bore extending axially entirely through the tubular member length.

14. The bore bolt assembly of claim 10, further comprising:
the proximal internal screw threading and the distal internal screw threading being portions of internal screw threading that extends axially entirely through the tubular member length.

15. The bone bolt assembly of claim 10, further comprising:
the tubular member exterior surface being a smooth cylindrical surface that extends axially entirely over the tubular member length.

16. A bone bolt assembly designed for attaching supporting plates and rods to bone, to hold adjacent bones stationary relative to each other, and to hold bone fragments together, the bone bolt assembly comprising:
a tubular member having an elongate, straight length with opposite proximal and distal ends, the tubular member having a center axis that defines mutually perpendicular axial and radial directions relative to the tubular member, the tubular member having an interior bore with proximal internal screw threading extending axially into the tubular member at the tubular member proximal end and the tubular member having an interior bore with distal internal screw threading extending axially into the tubular member at the tubular member distal end, the tubular member also having a cylindrical exterior surface that extends entirely over the tubular member length and is dimensioned for axially directed insertion through a hole drilled in bone;
a proximal bolt that is removably attached to the tubular member at the tubular member proximal end, the proximal bolt having an axial length with a cylindrical exterior surface with external screw threading at one end and having a head at an opposite end, the external screw threading being complementary to the tubular member proximal internal screw threading and the external screw threading being threaded inside the proximal internal screw threading in removably attaching the proximal bolt to the tubular member at the tubular member proximal end;
a distal bolt that is removably attached to the tubular member at the tubular member distal end, the distal bolt having an axial length with a cylindrical exterior surface with external screw threading at one end and having a head at an opposite end, the external screw threading of the distal bolt being complementary to the tubular member distal internal screw threading and the distal external screw threading being threaded inside the distal internal screw threading in removably attaching the distal bolt to the tubular member at the tubular member distal end;
the proximal bolt head and the distal bolt head each being adapted to attach a the tubular member to at least one of
a spinal instrumentation plate and a spinal instrumentation rod.

17. The bone bolt assembly of claim 16, further comprising:
the interior bore extending axially entirely through the tubular member.

18. The bore bolt assembly of claim 16, further comprising:
the proximal internal screw threading and the distal internal screw threading being portions of internal screw threading that extends axially entirely through the tubular member length.

19. The bone belt assembly of claim 16, further comprising:
the tubular member exterior surface being a smooth cylindrical surface that extends axially entirely over the tubular member length.

\* \* \* \* \*